United States Patent [19]
Zimmermann et al.

[11] Patent Number: 6,117,849
[45] Date of Patent: Sep. 12, 2000

[54] S-(+)-ADENOSYLMETHIONINE AND 3'-AZIDO-2', 3'-DIDEOXY-NUCLEOSIDE COMPLEXES AS POTENT INHIBITORS OF HIV-REPLICATION

[75] Inventors: Kurt Zimmermann, Herborn-Seelbach; H. Heinrich Paradies, Iserlohn, both of Germany

[73] Assignee: Symbio Herborn Group GmbH & Co., Herborn, Germany

[21] Appl. No.: 08/911,516

[22] Filed: Aug. 14, 1997

[30] Foreign Application Priority Data

Aug. 14, 1996 [DE] Germany .................. 196 32 823

[51] Int. Cl.$^7$ .................................. A01N 43/04
[52] U.S. Cl. ............................. 514/45; 514/42; 514/43; 514/46; 514/47; 514/48; 514/49; 514/50; 514/51; 514/885; 536/27.14; 536/27.31; 536/28.2
[58] Field of Search .................. 514/45, 46, 47, 514/48, 49, 50, 51, 42, 43, 885; 536/27.14, 27.31, 28.2

[56] References Cited

U.S. PATENT DOCUMENTS 4,242,505 12/1980 Kawahara et al. .
4,724,232  2/1988 Rideost et al. .
4,880,782 11/1989 Eckstein et al. .

FOREIGN PATENT DOCUMENTS 0 516 660 B1  8/1993  European Pat. Off. .

OTHER PUBLICATIONS

Vogel's Textbook of Practacal Organic Chemistry, Fifth Edition (Wilet,, New York, 1989), pp. 120–131.
ROMPP Chemie Lexikon, Ninth Edition (Georg Thieme Verlag, Stuttgart, 1992, pp. 4055–4056.
Fabianowska–Majewska et al., "Effects of Novel Anti–Viral Adenosine Analogues on the Activity of S–Adenosylhomocysteine Hydrolase from Human Liver", *Biochemical Pharmacology* 48:5;897–903 (1994).
May, "A Novel Antiviral Strategy for HIV Infection", *Medical Hypotheses,* 40:93–94 (1993).
Wolfe et al., "S–Adenosyl–L–homocysteine Hydrolase as a Target for Antiviral Chemotherapy", *Journal of Medicinal Chemistry,* 34:5:1521–1530 (1991).

*Primary Examiner*—James O. Wilson
*Attorney, Agent, or Firm*—Skjerven, Morrill, MacPherson, Franklin and Friel

[57] ABSTRACT

Molecular Complexes, comprising of S-(+)-adenosylmethionine and 3'-azido-2',3'-dideoxy nucleosides are prepared, and shown to have synergistic inhibitory effects on the replication of human-immunodeficiency virus 1 & 2 in vitro and in vivo, particularly on the reverse transcriptase, and having a high therapeutic index.

23 Claims, 6 Drawing Sheets

S-(+)-ADENOSYLMETHIONINE AND 3'-AZIDO-2', 3'-DIDEOXY-NUCLEOSIDE COMPLEXES AS POTENT INHIBITORS OF HIV-REPLICATION

BRIEF SUMMARY OF THE INVENTION

Molecular Complexes between S-(+) adenosylmethionine (SAM), which is a (+)-5'-[(3-amino-3-carboxypropyl)methylsulfinio]-5'-deoxyadenosine, and 2',3'dideoxy nucleosides having in the 3'-position an azido group have been synthesized, and found to be active in inhibiting the HIV replication in vitro as well as the reverse transcriptase of the human immunodeficiency virus 1 & 2 in vivo when in their appropriate stereochemical form. These complexes exhibit significant and sustained increase in the immune system marker CD4$^+$ in patients receiving the molecular complex compared to those e.g. receiving 3'-azido-2',3'-dideoxy-thymidine (AZT) alone. HIV-patients receiving one of the disclosed complexes also had lower HIV levels. This is supported by evaluating the levels of cytokines, e.g. IL-β, IL-2 and IL-6 as well as interferon-γ, and of the core protein p24. The biological responses of the complexes are e.g. documented by in vitro experiments of lymphocyte cultures which have been infected with HIV, and inhibitory effects on the reverse transcriptase (RT) revealing a high therapeutic index of approx. 7000 considering cytotoxicity, and an inhibitory constant of RT for the e.g. S-(+)-adenosylmethionine-AZT complex of 180 nM, with a Michaelis-Menten constant of 670 nM which was noncompetitive with respect to deoxyadenosine triphosphate or deoxyguanosine triphosphate, respectively, and having a $k_{cat}$ of 1.5 min.$^{-1}$ or 2.5 min$^{-1}$, respectively under the assay conditions.

The new synthesized complexes between SAM in the presence of OH$^-$ or Cl$^-$, respectively, and 3'-azido-2',3'-dideoxy nucleosides exhibit beneficial and favorable effects in treating HIV-infected patients, not only due to their synergistic response to the presence of AZT and SAM, respectively, but mainly due to the superior pharmacokinetics with respect to AZT when administered alone, and the efficacious treatment of the neurological disorder due to the absence of SAM or any other biological methyl donating compound including any suitable enzyme systems. Furthermore, the differences in the $k_{cat}$ and $K_M$ of the molecular complexes with regard to the RT enzyme system and AZT or SAM separately reveal a complete different molecular entity than the components of the complexes alone.

The new synthesized molecular complexes are characteristic of those for cationic π complexes revealing no typical Watson-Crick or Hoogsteen hydrogen bonding patterns between the bases of SAM and the azido-nucleosides as expected as A-T base pairing. However, Coulombic attractive forces between the sulfonium group and the partially polarized azido group of the nucleoside dominate the structures in the crystalline state and in solution, proving them as salt-like assemblies or ion pairs rather than typically covalent structures. We observe two structures with respect to the formation of the molecular complexes between SAM and the 3'-azido-2',3'-dideoxynucleosides: One structure contains the OH$^-$ or the Cl$^-$, respectively, as the building block, whereas the second one is devoid of the cations OH and Cl. Both complexes, with the SAM OH or the SAM Cl, as a building block, and ddN N≈N$_3$ as the other one, are water-soluble and stable at pHs between 6.5–8.5 between temperatures of 5° C. and 40° C., quite different from the common salts of SAM, which decompose at temperatures above than 20° C. as noticed by UV-spectroscopy and HPLC-analytieal techniques.

FIELD OF INVENTION

The present invention relates to a process for preparation of molecular complexes between S-(+)-adenosylmethionine (SAM), also known as "active methionine", and 3'-azido-2',3'-dideoxy nucleosides (ddN≈N$_3$) in their favorable stereochemical arrangement as opposed to other ddN-nucleosides or ddN≈N$_3$ respectively, having no biological activities due to an unfavorable stereochemical conformation. The described molecular compounds are suitable for treating HIV-infected persons as well as for patients which show symptoms of the AIDS-related complex (ARC), including their neurological disorders developed in the course of their disease. In-vitro and in-vivo studies of these complexes reveal a noncompetitive inhibition of the HIV-reverse-transcriptase a favorable bioavailability with respect to the 3'-azido-2',3-dideoxy nucleosides due to the stability of these complexes in acid and moderate alkaline solution, and temperature insensitivity when compared to SAM or known SAM salts, respectively.

BACKGROUND OF THE INVESTIGATION

Despite remarkable efforts provided in biology, virology and drug research including molecular modeling during the first decade after the initial description of AIDS in 1981, two drugs only, e.g. 3'-azido-2',3'-deoxythymidine (AZT, Retrovir, Zidovudine) and 2',3'-dideoxyadenosine (Didanosine, Videx) are approved for the treatment of AIDS patients and AIDS-related complex (ARC) as referenced by Mitsuya, H. et al., Proc. Natl. Acad. Sci., USA, 1985, 82, 7096–70100; Mitsuya, H., & Broder, S., Proc. Natl. Acad. Sci., USA, 1986, 83, 1911–1915). Both compounds are 2',3'-dideoxynucleoside analogues and most widely used as antiviral (retroviral) agent in both single and combination strategies for the treatment of acquired immunodeficiency syndrome (AIDS). Both compounds must be phosphorylated intracellularly to their 5'-triphosphate derivatives to interact with their target enzyme, the HIV-associated reverse transcriptase (RT). At the RT-level, the dideoxynucleoside triphosphates (dNTPs) can act as either competitive inhibitors preventing the incorporation of the natural substrates (dNTPs) or alternate substrates incorporated into the growing DNA chain. Furthermore, their incorporation leads to termination of the DNA chain since they do not process the 3'-hydroxy necessary for chain elongation. Another principle mode of infection by the human immunodeficiency virus of types, e.g. 1 and 2 (HIV-1 & HIV-2) involves the interaction of the HIV envelope protein gp 120 with CD4, a molecule on host lymphoid cells (see Ne .g. Dalgeish et al., Nature, 1984, 312, 763; Jameson, B. A., et al., Science, 1988, 240, 1335; Collman,R., et al., J. Virol., 1990, 64, 4468). Moreover, the susceptibility of many CD4 negative cell lines to HIV infection, however, suggests the presence of an alternative entry pathway according to e g. Clapham, P. R., et al., Nature, 1989, 337, 368; McKeating, J. A., et al., Nature, 1990, 343, 659. Other key factors regulating replication of the HIV are, apart from the RT with the three recognized enzymatic activities, i.e. the RNA dependent polymerase, DNA-dependent polymerase and the ribonuclease H, are the protease (PR) and the integrase, which are also essential for replication. The design of potent and structurally diverse HIV PR inhibitors has emerged over the past few years and has exemplified varying chemical templates, stereochemical complexity and molecular recognition properties in binding to the target enzyme, resulting in a clinically effective HIV-PR-inhibitor (see Thaisrivongs, S., Report Med. Chem., 1994, 29, 133 and references therein; Chang, H. E. J., Physicians Assoc. AIDS Care, 1994, and references therein). Also avenues for the treatment of HIV infection other than RT and PR inhibition have become evident over the last years. Plant alkaloids which modify the glycosylation of gp 120 inhibit the infectivity of HIV (Tyms, A. S. et al., Lancet, 1987, 11, 1025; Walker, B. D., et al., Proc. Natl. Acad. Sci., USA, 1987, 84, 8120) as well as castanospermine which is believed to excert its antiviral effect by reduction in virus infectivity and reduction in cell-to cell spread of the virus by inhibition of cell fusion events.

Very recently, Grundmann & Rübsamen-Weigmann reported in their patent, EP 0 516 660 B1 (1993), entitled "Use of S-adenosylmethionine as an agent against infections by retroviruses", an in-vitro inhibition of RT with notably inhibiting concentrations of approximately 100–200 $\mu$g/mL of S-adenosylmethionine (SAM) when administered as the tosylate-bis-sulfate salt applying lymphocyte cell cultures prepared from the umbilical cord of newborns. These lymphocyte cultures were inoculated with HIV taken from blood of an AIDS patient. The disclosed inhibitory concentrations of SAM is meant as the apparent concentration of SAM, which inhibits under their in vitro assay conditions 50% of the RT activity. Recalculations of the inhibitory effect of SAM on their RT would led us to an apparent $K_i$ value of approx. 200–250 nM after suitable corrections for the presence of dithiothreitol, DTT, which have to be applied. Inhibitory experiments using DTT, e g. for protecting sulfhydryl groups of the enzyme (RT), in their assay have to be omitted or corrected for, respectively, since DTT act as a strong reducing agent, particularly for SAM or SAM-tosylate-bis-sulfate which potentiates the reduction due to the sulfonium group which is being reduced to the sulfinium group, or to S-S-complexes comprising of SAM and DDT, respectively. Therefore, the apparent efficient inhibitory concentrations of SAM can well be lower than the measured ones. Note, the determined inhibitory concentrations are not the ones which can be correlated to the ones according to Michaelis-Menten kinetics. At least similar findings with respect to treatment of AIDS-patients revealing strong neurological disorder due to HIV-infection are disclosed in the European Patent Application 0 482 493 A2 by Bioresearch S.p.A. However, their study selected SAM and a derivative of tetrahydro-folic acid as the pharmaceutical ingredient administered a dose of 500 mg/kg/day parenteral including 0.5–1.0 mg/kg/day 5-methyl-tetrahydro-folic acid as a supplement. Basically this disclosure is concerned with the AIDS-induced neurological disorders in patients without addressing the importance of action of SAM on the RT as shown previously by Grundmann & Rübsamen-Weigmann. This view is endorsed through experiments conducted with 5-fluoro-deoxy uridylate (F-dUP) or the corresponding nucleoside, respectively, which is known as a powerful inhibitor of the thymidilate synthetase which uses a methyl group from a tetrahydrofolate species to synthesize TMP. In applying the in vitro assay for inhibition of RT in the presence or absence of F-dUP or F-dU the same $K_i$ value for SAM is obtained as determined by Grundmann & Rübsamen-Weigmann. This is a strong support that F-dU has no influence on the inhibition of RT, also no significant inhibition of the RT has been detected in the presence of 5,6,7,8-tetrahydropteridine (THF), a constituent of folinic acid or $N^5$, $N^{10}$-methylene-6-[$^3$H]-THF with the RT enzymes. This establishes clearly the mode of action of SAM on the RT in an inhibitory sense which the Bioresearch Patent failed to disclose since the above mentioned experiments reveal no involvement of THF in the inhibition of RT.

As outlined above there are several drugs that have shown to be potent for the treatment of HIV infection. But, as it is known for e g. AZT, any of these drugs have serious dose-limiting toxicities, and most importantly HIV develops resistance against these drugs after a certain period of time (see e g. Richman, D. D. et al., Acquired Immune Defic. Syndr. 7,189, 1994; Richman, D. D., Antimicrob. Agents. Chemother., 37, 1207, 1993; Montanier, L. S., et al. AIDS 7, 189, 1993. Furthermore, in light of the limited benefits when HIV infected patients were treated with anti-retroviral compounds, the likely causes of these limited benefits are possibly the emergence of drug resistant strains during monotherapy. The potential use and mechanism for sustained anti-retroviral efficacy is documented for example very recently for the AZT-3TC combination therapy (3TC= [−]-2'-deoxy-3'-thiacytidine) according to Larder, Kemp & Harrigan (Science 269, 696–699, 1995). These authors showed that an AZT-3TC combination therapy resulted in a markedly greater decrease in serum HIV-1 RNA concentrations than treatment with AZT alone, even though valine-184 mutants rapidly emerged. In addition, AZT-3TC coresistance was not observed during extensive in vitro selection with both compounds.

DETAILED DESCRIPTION OF THE INVENTION

Figure 1:
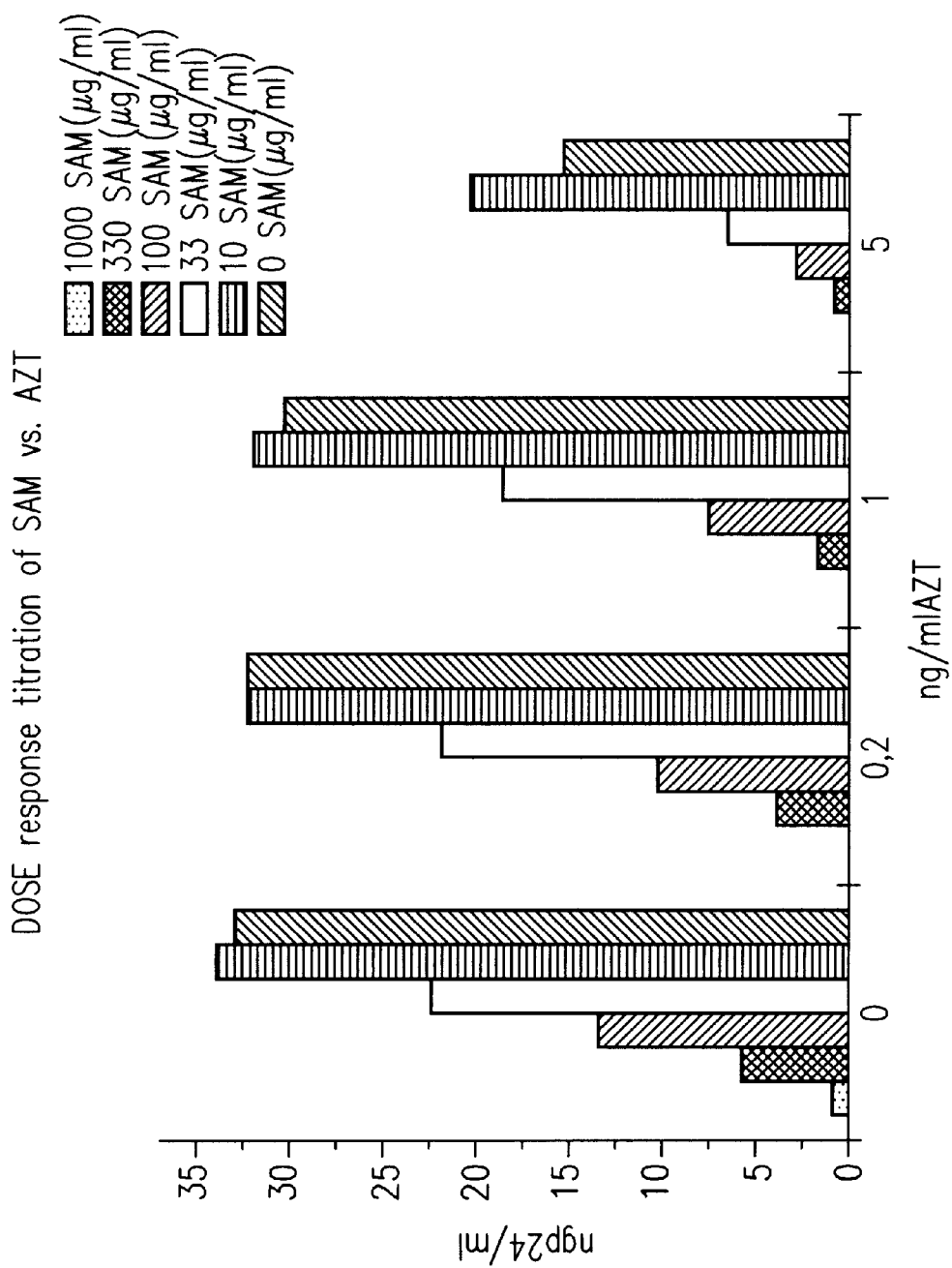
FIG. 1 displays concentration of viral core protein p24 in lumphocte cultures as function of SAM and AZT concentration.

This invention relates to molecular complexes comprising of SAM having the chemical formula as shown in scheme 1, and 3'-azido-2',3'-dideoxy nucleosides (ddN≈$N_3$ and analogs with bases B, encompassing the pyrimidine bases thymine (T) or uridine (U) and cytosine (C), the purine bases adenine (A), guanine (G) and (I) for hypoxanthine (see scheme 1). Scheme 1 shows also the chirality of the designated asymmetric centers of the compounds building the molecular complexes, including for the sulfur atom. The nucleosides can contain in 2' position either a fluorine or a hydrogen. These nucleoside analogs contain 3'-azido-2'-dideoxy ribose surrogates according to formula II in scheme 1, and the base composition as listed include both L-(−)- and D-(+)-enantiomers in complex with SAM for AZT, GZT and UZT, respectively.

We have found that these complexes can produce favorable and synergistic effects, or at least additive anti-retroviral activity against HIV without a concomitant increase in toxicity in vitro. In addition we discovered that these compounds influence the release and control of interferon-γ. Furthermore, it has been found that the cytokine biosynthesis for IL-β, IL-2 is influenced by SAM after stimulation of the lymphocytes through phytohemagglutination but not by ddN≈N₃, but enhanced significantly in the presence of the molecular complex of SAM-AZT. Furthermore, we found that the anti-retroviral activity of SAM when in complex with ddN≈N₃ against RT is also potentiated by the granulocyte-macrophage colony-stimulating factor in vitro. In this respect, the anti-retroviral activity of 3'-azido-2',3'dideoxyuridine (scheme 1) was also potentiated by the above mentioned cytokines in vitro when in complex with SAM, so enlarging the therapeutic ratio in vitro and in vivo for the whole class of 3'-azido-2',3'-dideoxynucleosides.

Furthermore, it was also found that SAM-ddN≈N₃ inhibits TPA (12-O-tetradecyanyl phorbol-13-acetate) stimulated replication of HIV in acutely infected cells, but in a different way as N-acetylcysteine (NAC) which is known to replenish intracellular glutathione concentrations. This inhibition is only seen by this molecular complexes, not by either components alone or given separately e.g. as a loose combination partly due to their different pharmacokinetic profiles, bimolecular targets, and differences in protein binding. Also, which in turn is different from NAC, SAM does not inhibit cytokine-activation of HIV expression in vitro, but it does in vivo and only in the molecular combination.

CHEMICAL DESCRIPTION OF THE COMPLEXES

Generally, the molecular complexes between SAM OH or SAM Cl, respectively, or SAM⁺and 3'-azido-nucleoside analog according to the formula ddN≈N₃ with the bases shown in scheme 1, part II, and sugar moiety as depicted in part III, can easily prepared by contacting SAM•HCl or the corresponding sulfate as SAM•HSO₄•H₂SO₄ (e.g. 1.0 nmol) with the stoichiometric amount of e.g. AZT at 20° C. in water (20 mL) under stirring in the presence of 1.0 mM AgNO₃ or an suitable anion exchanger, Cl⁻ →OH⁻ e.g. Dowex (e.g. starting with Dowex-Cl, 50–100 mesh, converted into the hydroxide) form under nitrogen atmosphere in order to avoid oxygen in excess for preventing oxidation of any kind of SAM. Upon separating the used Dowex-Cl⁻/OH⁻ anion exchanger, or the AgCl from the reaction medium by filtration or by low speed centrifugation (rpm~500–1000) the clear transparent aqueous solution can either be concentrated upon evaporation of water, or precipitated in the presence of 2-propanol or a mixture (40/60 w/w) of ethanol and n-propanol. Another suitable solvent is also a calculated amount of BaCl₂ in an N₂-atmosphere in order to avoid dimerization of (+)-SAM. The nucleoside analog can be dissolved in either acetonitrile/petrolether, which can also be used for crystallization or recrystallization of the molecular complexes, or in 2-isopropanol containing 20% (v/v) water i.e. for recording UV-spectroscopic properties Normally the material crystallizes as a fine precipitate which upon cooling at 5° C. crystallizes as thin plates, suitable for X-ray diffraction investigations, and various optical investigations for determining chirality and other stereochemical properties. Upon recrystallization of the material in 50% (w/w) EtOH and 50% (w/w) water, the pure complexes can be obtained also having melting points in the range of 170 to 194° C., which are much higher than found fort the building blocks comprising of SAM and the 3'-azido nucleoside analogs.

The 3'-azido-2',3'-deoxynucleosides can be prepared according to standard procedures, particularly to the one disclosed by Goulaouic, et. al. (Goulaouic, C.; Adams, D. R.; Chiaroni, A.; Riche., C.; Grierson, D. S.; J. Org. Chem. 58, 3030, 1993).

The molecular complexes can also prepared by using the (+)-SAM-bis-sulfate as the starting material which is readily soluble in water (20° C.) upon addition of solutions consisting of 50% EtOH and 50% of water, or neat water and adding an ethanolic solution of the equivalent amounts of the 3'-azido-2',3'-dideoxynucleosides. By removing the precipitate the supernatant contains the desired molecular complex comprising of SAM and ddN≈N₃ in almost quantitative chemical yield and high optical purity, as assessed by NMR using chemical shift reagents to determine the chirality, and the specific optical rotation, [α].

According to IR and X-ray diffraction analysis of single crystals of the molecular complex of SAM≈AZT, we noticed no hydrogen bonding between of the thymine base of AZT with the adenine moiety of SAM as Watson-Crick or Hoogsteen base pairing, as one could anticipate. The structure can be best described as an cationic π-complex with strong Coulomb attractive forces between the azido group and the positively charged sulfur. Very similar results are to be seen with the other complexes according to scheme 1 with the bases cytidine, inosine and uridine, respectively.

In addition to this sort of electrostatic bonding dominating the molecular packing of the solid material we noticed also hydrogen bonding between adenine bases of two SAM molecules which are connected to each other rather than thymine-adenine base pairing from a different AZT molecule in the crystalline state. The observed base pairing is very similar to the one observed in deoxyadenosine monohydrate (Watson, D. G., Sutor, D. J., & Tollin, P., Acta Crystallogr.,19, 111, 1969). Of particular interest is the hydrogen bonding between the R-methionine moiety and the adenine, guanine or the inosine base, and quite surprisingly the hydrogen bonding between the 3'-azido-nucleoside analogs between nitrogen-(1) of the pyrimidine bases and the methionine, respectively. On the basis of this hydrogen bonding pattern of these complexes the enantiomeric R-methionine moiety of both classes of complexes, either with purine or pyrimidine bases, takes the zwitterionic form, e.g. the N (α) atom carries three hydrogen bonds with the same molecule, e.g. SAM, and three also for the corresponding 3'-azido-nucleoside.

A different situation arises when the molecular complexes are crystallized from watery solutions yielding materials containing different amounts of water as hydrates according to thermogravimetry and differential thermal analysis as well as X-ray diffraction powder patterns. The water molecules which average six e.g. for the SAM-AZT complex and eight for the SAM~ddu≈N₃ molecular complex, are located in large interstitial gaps, and they stabilize the molecular packing of the SAM molecules in the crystal lattice via attractive forces due to the interaction between the azido group and the positively charged sulfur of SAM, respectively, as well as through extensive hydrogen bonding with base nitrogen, ribose hydroxyl oxygen, and water oxygen atoms. There is solely no typical base pairing according to Watson-Crick or Hoogsteen to be seen.

The dehydration process as investigated by means of thermal analysis consists at least to two processes: two water molecules as estimated from the weight loss were first dehydrated at approx. 35° C.; the remaining water molecules were dehydrated at about 110° C. The former water molecules are loosely bound within in the crystal lattice, having a similar importance as it has been noticed for antiviral cationic surfactants (Paradies, H. H., Acta. Crystallogr.,C49 744–748 1993) and a similar molecule of the pteridine class in the presence of water & dimethylsulfoxide (Dahl et al., J.Pharm Sci.,78, 598,1989). The fairly hydrated species which is found also in solution due to NMR results are probably the one who is dominating the anti-retroviral effects. It is obvious that dehydration is effecting the structure considerably since it can be noticed that these materials re-hydrate in a time dependendent manner by picking up water molecules or water-like components as ethanol or even DSMO, indicating that water is essential for the structural integrity of these molecular complexes. The investigation of the dehydration process of the molecular complexes, particularly those comprising of SAM OH and 3'-azido-2',3'-dideoxythymidine or uridine, respectively, leads to an understanding observation of the chemical nature of the complexes with respect to the fate of the OH or Cl. Preparing the complexes in the presence of $NH_4HCO_3$ instead of SAM OH or SAM Cl, with subsequent drying at 50° C. in vacuo over CaCl, (drying pistol) or over $CaCl_2$ in a $N_2$ atmosphere in a desiccator for a period of time of 2–4 hours, yielded molecular complexes of the type SAM-ddN≈$N_3$, e.g. SAM-3'-azido-2',3'-dideoxythymidine, containing no OH or Cl, respectively. On a large scale these complexes can be manufactured from a ethanolic solution of SAM Cl or SAM OH (100% EtOH) contacting with a ethanolic solution of e.g. 3'-azido-2',3'-dideoxynucleosides in the presence of stoichiometric amounts of $AgNO_3$ (also in 100% EtOH) under stirring at 20° C. and $N_2$. The precipitate is filtered off and discarded, the supernatant containing the complexes in the absence of any Cl or OH, can be concentrated by rotary evaporation until a fine precipitate occurs. Upon standing in EtOH at 5° C., thin platelet like crystals appeared. The same results can be obtained conducting the removal of the counterions in the presence of a slurry of $Ag_2O$ in EtOH under $N_2$, avoiding any oxidation.

The products are water soluble, temperature stable between −5° C. and 50° C., showing no deterioration of either R-(+)-SAM or the ddN≈$N_3$ analogs in contrast to the known salts of R-(+)-SAM, resulting in a highly stable pharmaceutical solid form when not using any inactive ingredients. The aqueous solutions of these compounds are also pH-stable between pH 5.0 to pH 8.5 (20° C. to 37° C., at constant ionic strength of 0.15 M) revealing no deterioration of either component, e.g. SAM and ddN≈$N_3$. Conductivity measurements do indicate the complex materials as ion pairs, not unusual for a fairly hydrated cation $(SAM)^{\delta+}$ and a less hydrated (solvated) polarized anion $(ddN{\approx}N_3)^{\delta-}$. This observation is supported also by conductivity experiments at very low ionic strength, or solvents having a different dielectric constant than water. According to NMR experiments (C-13 and H-1,H-2) as well as FTIR data a dramatic re-ordering in $H_2O$ of these molecular complexes can be noticed which might be important for treating HIV and failures in man according to the ARC: the bioavailability and the penetration of the blood-brain barrier in man of these molecular complexes is enhanced since the inherent nature of these complexes follow a different mechanism when administering the drugs alone and separately including in different order, e.g. AZT first, SAM second or vice versa, respectively. Due to the presence of the “vehicle-like” function of SAM the appearance of e.g. AZT at higher concentrations in plasma as well as in the cerebrospinal fluid (CSF) can be explained i.e. on the basis of hydration of the molecular complex, protecting the hydrophobic site of the azido nucleoside analogs in a pocket of the SAM molecular complex by extensive hydrogen bonding with the water molecules and the attractive electrostatic forces within the highly solvated entity. Note: This finding is very important since it explains the prolonged SAM appearance in the cerebrospinal fluid together with e.g. AZT, which is a definitely desired effect for treatment of patients suffering from ARC. The same reasoning applies for the diffusive transport of ddN≈$N_3$ in the presence of SAM into the red blood cells by improving the biotransport through plasma membranes or lipid barriers, which is faster by an order of three as it can be shown in a system for fully synthetic or natural occurring vesicles (Paradies, H. H., J.Phys.Chem., 90, 5956, 1986), or for erythrocytes, respectively. Furthermore, SAM crosses the blood-brain barrier slowly but with significant accumulation in the CSF as discovered after administration of 200 mg or 400 mg, respectively, SAM parenteral for an HIV infected patient. Moreover, it was found that the peak of the CSF levels of SAM is relative to the one in the plasma lower and more prolonged for healthy patients than for patients having neurological disorders including those belonging to the ARC.

Note: SAM has almost no significant protein binding, only of the order of 3–5% as determined. However, in case for patients infected with HIV (N=3) which belong to the group of progressors (in typical progressors, within weeks of HIV infection, the virus load falls coincident with the induction of anti-HIV cellular and humoral responses, whereas rapid progressors show a rapid decline in $CD4^+$ peripheral blood cell levels, usually within 2 to 3 years after primary HIV infection. Nonprogressors have high levels of $CD8^+$ $CD38^+$ cytotoxic T cells), which had no detectable levels of SAM (!), we determined SAM levels after 30 minutes of 600 ng/mL, after one hour 610 ng/mL, and after 4 h 300 ng/mL after administration of 200 mg SAM as-tosylate•$HSO_4$•$H_2SO_4$. The values of the molecular complex of SAM~AZT, e.g. 400 mg SAM as active ingredient equivalent 250 mg AZT as active ingredient (note, the molecular weights of AZT and SAM, respectively, are almost equal in mass) yielded the following values: SAM after 1 h, still 600 ng/mL (±30 ng/mL), AZT (1 h) 0.25 $\mu$g/mL almost 50% of the one found in the plasma of 0.543 $\mu$g/mL (±15 $\mu$g/mL). The corresponding data obtained for AZT alone at a dose of 250 mg AZT were found to be 0.01 ng/mL, plasma concentration peaks at 2.5 $\mu$g/mL under the same conditions. It is worth mentioning that the molecular complexes as shown here for SAM-AZT, similar findings can be reported for the corresponding complex between SAM and UZT, revealed actually a dose reduction of AZT of approx. 30% when administered as a complex with SAM, or administering the approved dose of 250 mg AZT at 4 h intervals on the basis of the drug half-life of 1 h will yield considerably (in the average of 25–30%) higher SAM and AZT levels in CSF and plasma. In addition we observe also a lower elimination rate for SAM, therefore a prolonged reservoir of SAM with respect to treating neurological disorder within the ARC symptom complexes, e.g. lymphocytic pleocytosis, malaise without meningeal signs, fever, flu, meningeal infections including the partial restoration of immunological functions. This includes also an increase in T cell lymphocyte counts and a decrease in frequency of chronic opportunistic infection as it has been observed in a comparable study of SAM≈ddN-$N_3$ complexes with e.g. AZT, and AZT alone. Due to the induced rapidly developing resistance to AZT by HIV and variants, these molecular complexes foil drug resistant HIV, where both compounds, e.g. SAM and AZT, respectively, interfere with the HIV enzyme RT. The synergistic effect of these molecular complexes as well as of SAM and AZT, has been tested in i.) an in-vitro screening system based on human peripheral blood lymphocytes which have been infected with HIV, and ii.) by an in-vitro system using RT as an indication for inhibition. One aim of this study was to determine whether SAM, when co-cultivated with low doses of AZT, reveal a synergistic anti-retroviral effect, or does SAM and low doses of AZT abolish the anti-retroviral effect of either SAM or reduce the anti-retroviral activity of AZT, or does it inhibit both. Another reason to test these molecular complexes is to make sure that the anti-retroviral effect is not only due to the azido-dideoxy nucleosides e.g.AZT, but also to verify that the cell toxicity is not enhanced due to this molecular complexes. For this purpose, SAM has been tested in a dose response titration ranging from 1000 $\mu$g/mL to 10 $\mu$g/mL final concentrations for the ability to inhibit HIV replication in de novo infected cells. Endpoint in this assay was the quantitative determination of the concentration of the viral core protein p24 as described by Mueller et al. (Mueller, Ch., Moritz, R., Prigge, G., Weitzel, D., Kunze, R., Kage, A., Koettgen, E., Fresenius Z. Anal. Chem.,330, 352–353, 1988). In addition SAM has been tested for the aforementioned concentrations in the presence of AZT at a final concentration of 0.2 ng/mL, 1.0 ng/mL and 5.0 ng/mL, respectively. The toxicity testing of cellular proliferation was performed according to J. Mosmann (J. Immunological Methods, 65, 55–63, 1983). Additional controls have been included to validate the dose response and in parallel experiments the cell proliferation tests were performed. All experiments were carried out in triplicate cultures, including those for the various concentrations of the molecular complexes tested.—The lymphocytes were infected with a standardized preparation of HIV-1 isolate of HIV IIB. The cells were sedimented by low speed centrifugation, the sediment resuspended in the assay buffer (standard), and the resuspended cells were inoculated by adjusting to the following conditions: 100 ng of viral core protein p24/mL and 3200 pg HIV RNA/mL, respectively. Normally $3\times10^8$ lymphocytes were suspended in 1 mL if the HIV inoculum, and incubated at 37° C. for 60 minutes. After washing the cells twice with 50 mL of culture medium the cells were resuspended at a concentration of $3\times10^6$ cells/mL in culture medium which contains 10 units/mL of human recombinant interleukin-2. 100 $\mu$L of this cell suspension were added to 100 $\mu$L of the pre-diluted solution of the compounds to be tested, without adding any salt or protein. The entire assay was cultivated in humidified atmosphere in the presence of 5% $CO_2$ at 37° C. After the 4th day of infection the viral replication was determined in the lymphocyte cultures. The end point of the titration was the determination of the viral core protein p24 in the supernatant of each of the lymphocyte cultures. 150 $\mu$L of the supernatant were removed and transferred to a vial containing 50 $\mu$L/well SDS at a final concentration of 0.08% (w/w). The concentration of the synthesized p24 by the HIV infected cells was determined according to Mueller et al., using recombinant p24 as a standard for calibration.

The results obtained clearly demonstrate that AZT and SAM inhibited HIV replication in a dose dependent response (FIG. 1). The Michaelis-Menten kinetics of these complexes or of the combination of the active ingredients of the complexes exhibit a bimodal response revealing two different inhibition constants, $K_{i(1)}$ and $K_{i(2)}$, respectively. However, when tested in combination or as a the molecular complex the effective inhibitory constant $K_i$, at 50% inhibition was determined to $K_{i(1)} \approx 1.5$ ng/mL and $K_{i(2)} \approx 15$ $\mu$g/mL for the combination, but for the molecular complex we compute values of $K_{i(1)} \approx 0.9$ ng/mL and $K_{i(2)} \approx 12.5$ $\mu$g/mL, respectively (p<0.005). The superficially close values obtained for the loose combination versus the one for the chemical complex are due to the same concentrations applied to the in vitro system with respect to SAM and AZT, respectively, since they have almost the same molecular weights, however, statistically different from each other. The statistical analysis strongly indicates for p<0.005 significantly lower inhibition constants over the loose combination of SAM and AZT, respectively, and for p<0.01 the inhibition constants are significantly higher than those ones for the molecular complex of SAM-AZT. The same results are obtained when administrating the two compounds separately in sequence after a lag time of 5 minutes to each other. The order, which one comes first, is not of importance, i.e. it does not change the outcome of the results. Moreover, the very unexpected low inhibitory concentrations for the molecular complex of SAM-AZT for inhibition of HIV replication (0.9 ng/mL and 12.5 $\mu$g/mL) vs. the ones for the loose combination of SAM & AZT can be reconciled under the aspect of dissociation upon dilution of the complex with time under the experimental conditions (steady state conditions). Since the molecular complex is not a covalent molecular entity rather than a structure held together by electrostatic and attractive forces including hydrogen bonding it is not surprising that the $K_i$-values obtained at a first inspection do look very similar, but they are not as shown by their statistical significance. This can easily be demonstrated by increasing the ionic strength of the culture condition of the T lymphocytes: The $K_i$-values of the molecular complex decreases to 0.6 to 0.8 ng/mL and 8 to 10 $\mu$g/mL, respectively, at an ionic strength of 0.075 M, whereas the loose combination of SAM and AZT, if administered together or separately within a period of time of 1 to 5 minutes, does not change the $K_i$-values as mentioned above at all. This can also be demonstrated by addition of human serum albumin: the inhibitory constants do not change with concentration with respect to the administered SAM-AZT complex, revealing low inhibitory constants $K_i$ of the order of 0.5 to 0.8 ng/mL and 10 $\mu$g/mL, respectively. In case of the loose or separate administration of SAM and AZT, $K_i$ values of AZT or SAM, which are much higher, are obtained.

The results obtained for the cell toxicity applying the aforementioned toxicity test of the molecular complex of SAM-AZT reveals a considerable of reduction of cell toxicity with respect to AZT alone. The cell toxicity, of the complexes were also determined using the proliferation test and assessed as the percentage of the controls versus the e.g. SAM-AZT complex, and compared with SAM alone. We notice an increase of the cell toxicity by approx. 35%, taking the determined values for SAM as: 20 mg/mL 13%; 2.0 mg/mL, 52%; 0.2 mg/mL, 77%; and 0.02 mg/mL 96%, respectively.

The second in-vitro test uses the enzymatic activity of RT, testing the kinetic and inhibitory action of the molecular complexes. The cloning of the RT in biologically active form made it possible to have large quantities of the RT enzyme available for these studies (RT from Sigma, lot # R 9376).

The steady state reaction conditions for RT are chosen that approximate physiological conditions are met: pH 7.45 (37° C.), ionic strength of 150 mM, routinely a buffer was employed consisting of 50 mM TRIS-HCl, 100 mM KCl, 5 mM $MgCl_2$, the addition of 10 $\mu$g/mL bovine serum albumin were included. DTT was omitted from the inhibition studies for SAM or SAM≈ddN-$N_3$ since it is known that AZT-5'-triphosphate is being reduced by DTT to 3'-amino-3'-deoxythymidine, so also all other azido compounds to amino derivatives substituted in the 3' position of the 2'-deoxyribose. The aforementioned precautions designed to avoid potential reduction of SAM in the presence of DTT are taken into accounts to preclude any distortions of the kinetic behavior of the RT enzyme in the presence of the various substrates e.g. as our molecular compounds. There is no deleterious effect on the RT activity in the absence of DTT as we proved by appropriate controls. However, RT assay conditions in the presence of 5 mM DTT and SAM or SAM≈ddN-N$_3$ complexes destroy SAM primarily because transsulfuration to DTT takes place under release of formed S-adenosylhomocysteine. As a result the inhibitory concentrations needed are higher than they actually have to be, so the K$_i$-values are tainted, and not very reliable. Table I shows the K$_i$-values measured for sonic compounds tested and relevant for this disclosure, also included are those for SAM•Cl, or SAM•tosylate•HSO$_4$•HSO$_4$, respectively, to demonstrate the above mentioned effect of DTT. The enzyme concentrations of RT was approx. 20 nM, T-P (template-primer) 150 mM and 25 μM of [$^3$H]-dNTP (assay conditions are modified fro those of Mayunder et al., J. biol. Chem.,263, 15657, 1988). Inhibitors are classed according to their effect they have on steady state kinetic parameters, k$_{cat}$ and K$_M$. As a result simple competitive inhibitors increase K$_M$ without affecting k$_{cat}$ whereas non-competitive inhibitors decrease k$_{cat}$ without influencing K$_M$. In case both parameters are effected to the same extent, then the inhibition is uncompetitive. In order to facilitate the difference between SAM kinetics and those for the molecular complexes we studied first SAM kinetics and subsequently the kinetics in the presence of the molecular complexes. According to the results obtained SAM can be regarded as a non-competitive inhibitor since k$_{cat}$ is decreasing without any influence on K$_M$. Since the kinetic reveals a bimodal response in a sense that we notice at low SAM concentrations, e.g. $^-$10 μg/mL, SAM acts as a competitive inhibitor since K$_M$ increases at almost constant k$_{cat}$. Furthermore, we noticed a non-competitive inhibition from a double reciprocal plot for inhibition of RT by SAM with rT-oligo(dT) as fixed at saturating concentrations with dATP as variable substrate. Similar experiments have been carries out with dGTP. At the two highest concentrations of SAM, used as tosylate•HSO$_4$ •H$_2$SO$_4$ or Cl, the intercept on the 1/S axis increases. These changes are statistically significant, suggesting a low affinity site on RT and a high one.—FIG. 2 shows the results obtained for SAM in the absence of DTT for an RT enzyme that resembles in the kinetic behavior almost the HIV-enzyme.

Figure 3:
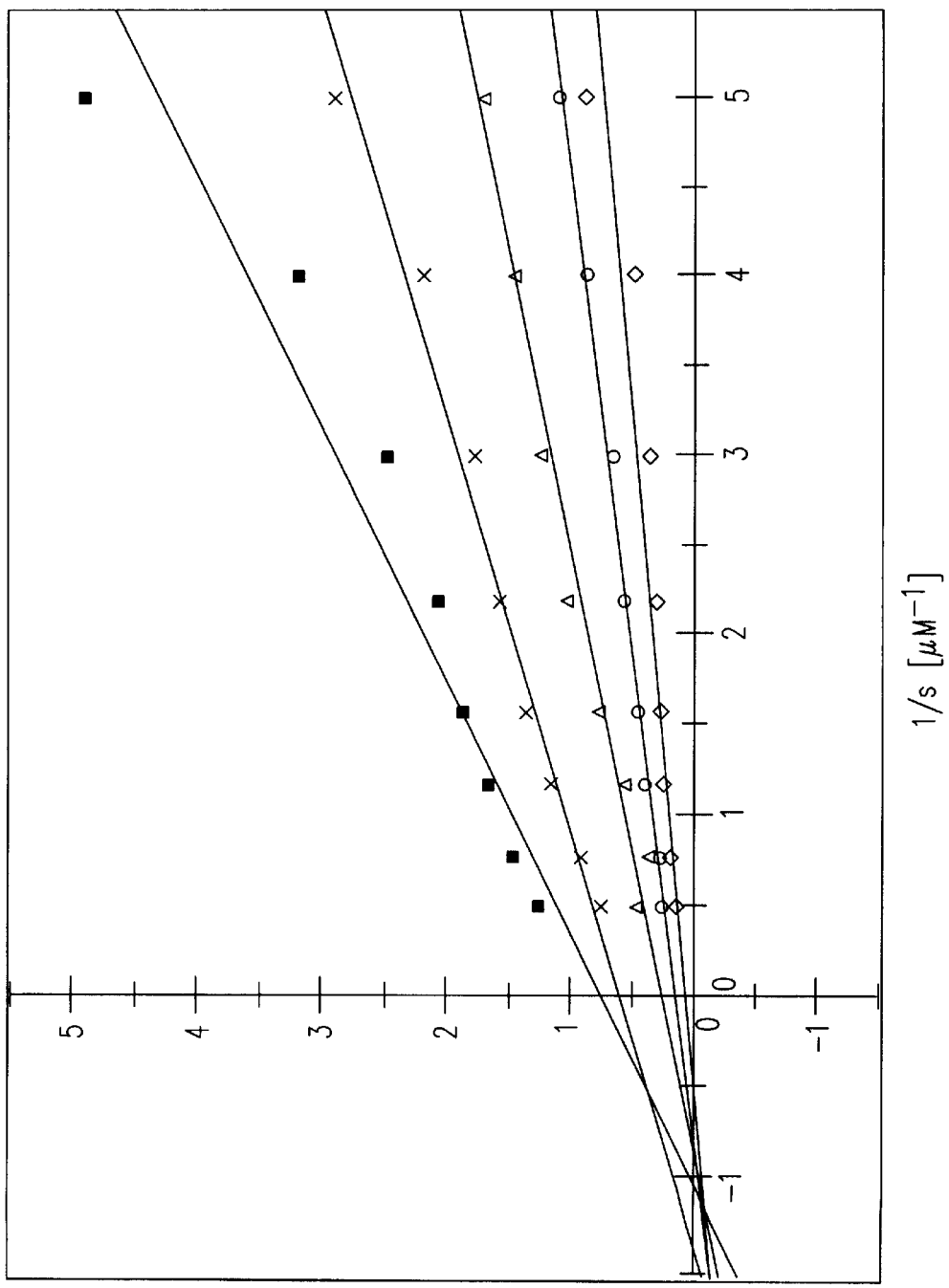
FIG. 3 is a double reciprocal plot for inhibition of RT by SAM-AZT complex.

However, inhibition is complete before saturation of the e.g. SAM-AZT complex occurred at these sites as seen in FIG. 3. A plot of the ordinate intercepts vs. concentration of SAM-AZT is linear, and yields a K$_i$ value of 180 nM. The Michaelis-Menten constant (K$_M$) under this condition was found to be 670 nM, and k$_{cat}$ for this system (RT-polymerase) was found of approx. 1.5 min$^{-1}$. Note the k$_{cat}$ value for AZT in this assay system is of the order of 1.5 sect$^{-1}$. Table I lists all other compounds tested in this system. The enzyme was assayed with 50 nM primer sites on poly (rA): oligo (dT), and variable concentrations of [$^3$H] dTP as substrates in a reaction mixture as described above at pH 7.5 (37° C.).

Figure 2:
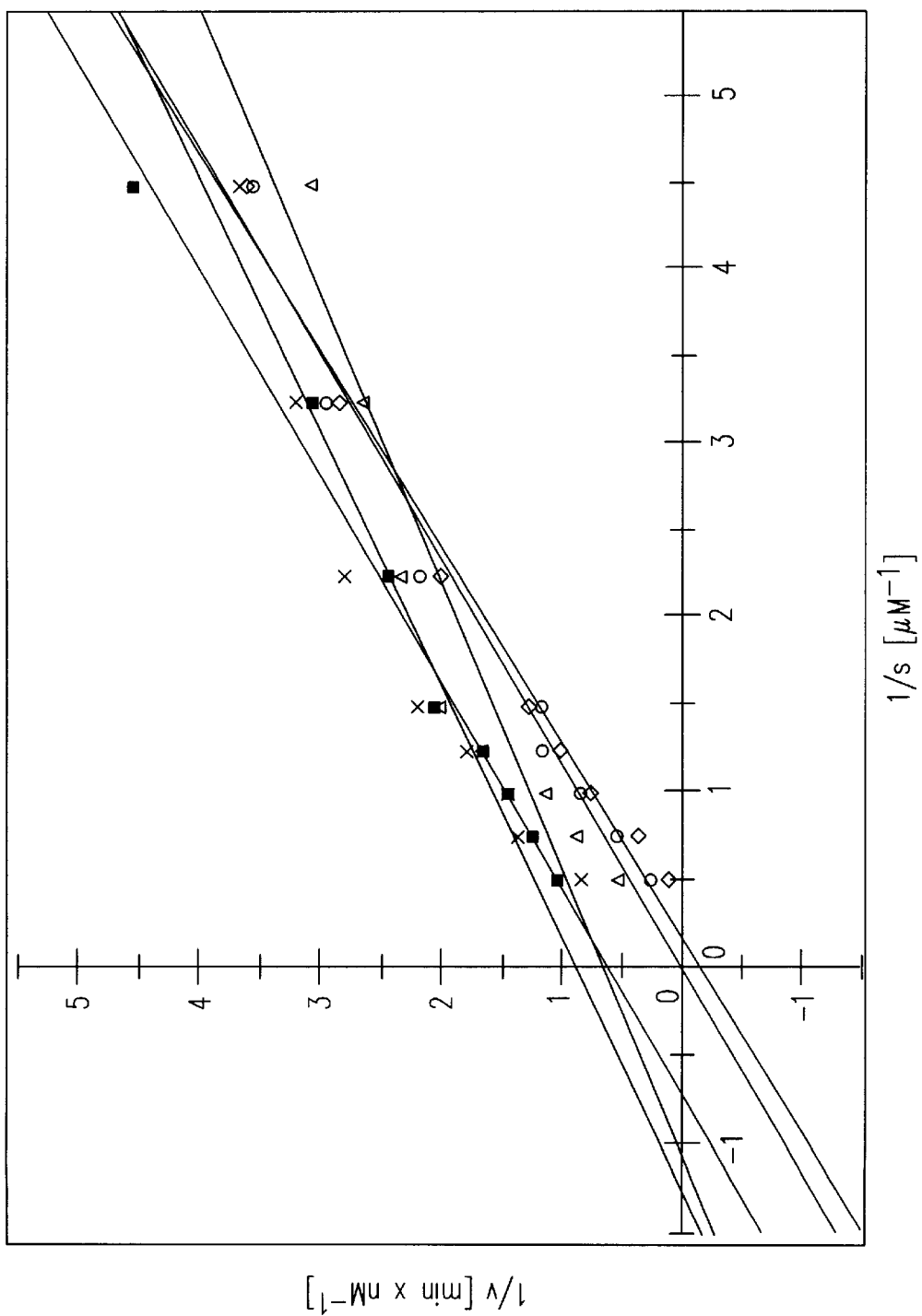
FIG. 2 is a double reciprocal plot for inhibition of RT by SAM.
Figure 4:
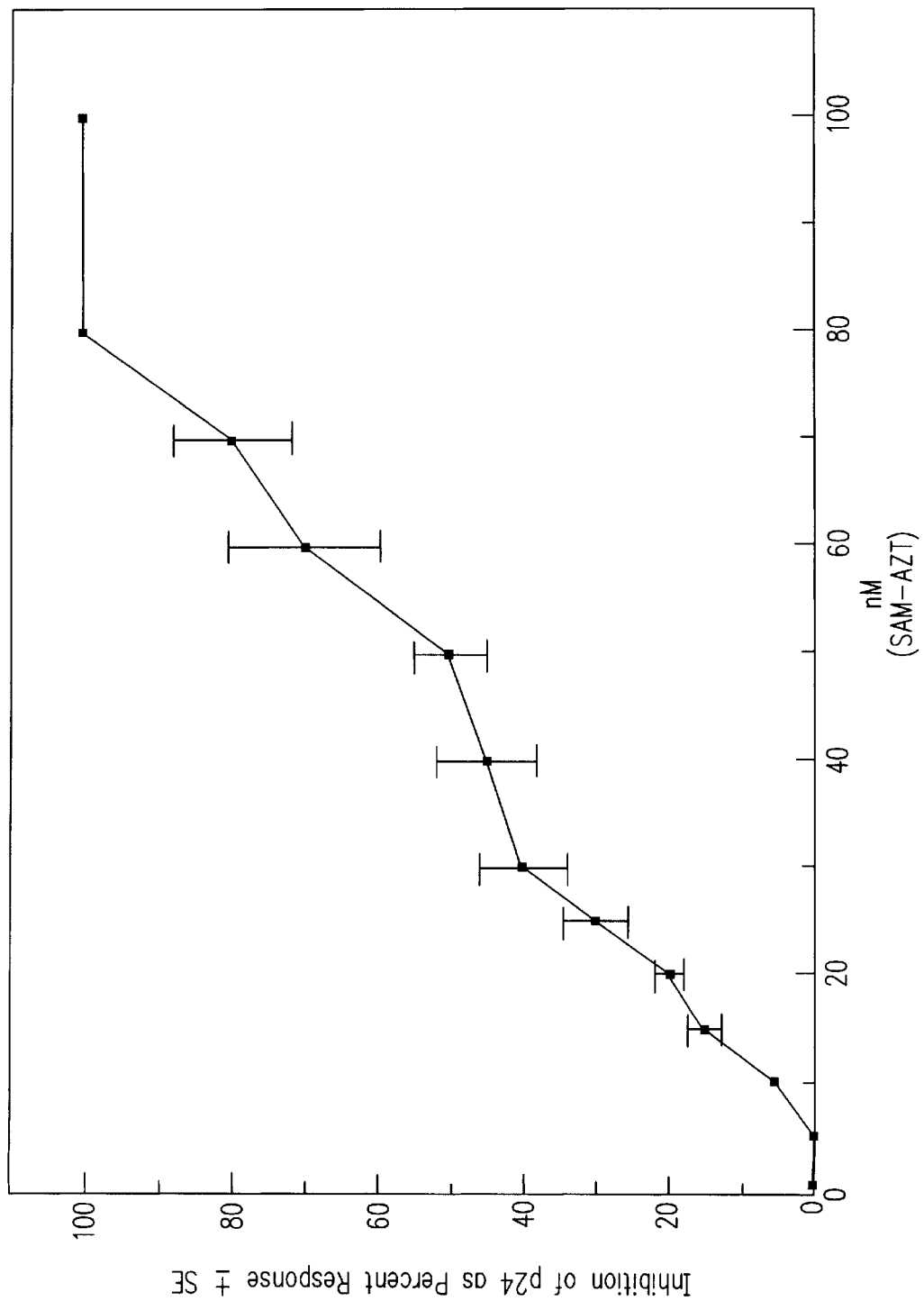
FIG. 4 demonstrates viability of T-cells in T-lymphocyte cell cutures as a function of SAM-AZT dose.
Figure 5:
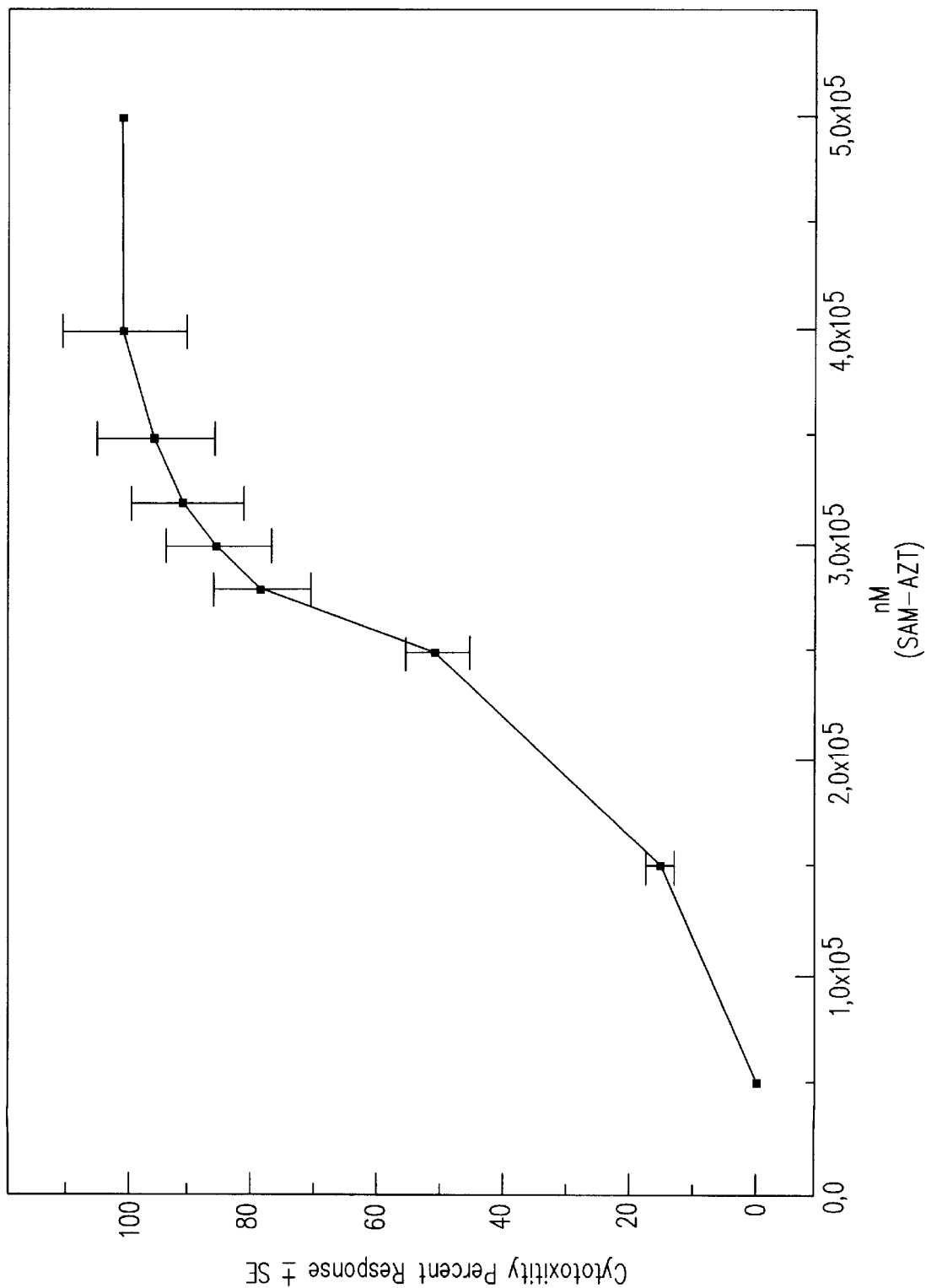
FIG. 5 displays cytotoxicity in T-lymphocte cell cultures as a function of SAM-AZT dose.
Figure 6:
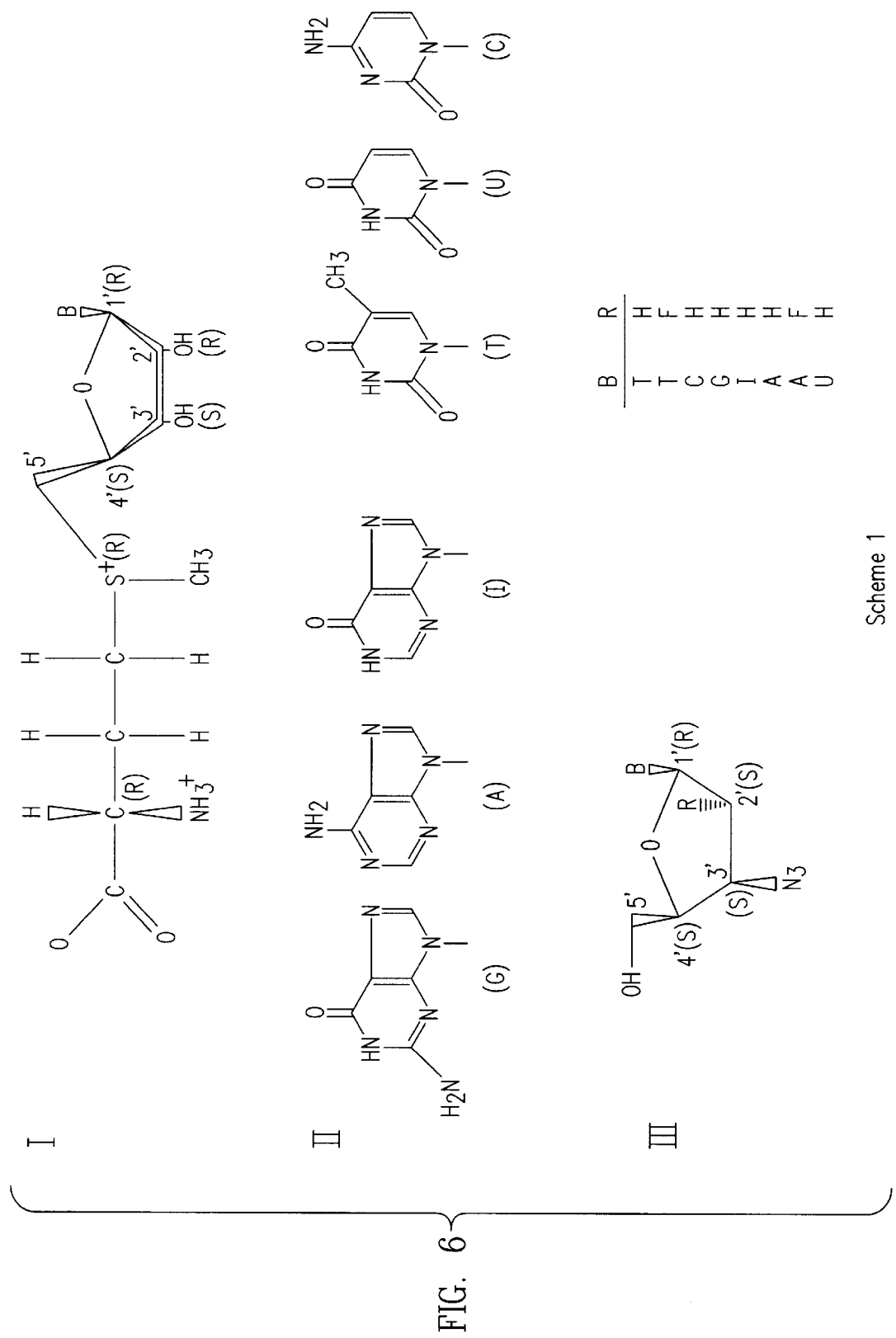
FIG. 6 illustrates (I) the chemical structure of a complex of SAM and ddN≈$N_3$, where the bases and sugar moiety of ddN≈$N_3$ are displayed in (II) and (III), respectively.

The effect of the molecular complex between SAM and AZT on HIV-replication, including the data obtained as listed in FIG. 1, as well as FIGS. 2 & 3, respectively, were tested in T-lymphocyte cell cultures monitoring viability of the T-cells and the IC$_{50}$ for demonstrating the therapeutic index of this molecular complex. The results obtained are shown in FIGS. 4 & 5. Interestingly, the IC$_{50}$, which has been calculated according to 100•[(control)-(SAM-AZT)]/(control) was found to be of the order of 50±10 nM with a maximum inhibition of 100% as determined by inhibition of the cytotoxic effect, and 10 nM with an I$_{max}$ as determined by inhibition of p24 production. Viability of the T cells was determined by means of a tetrazolium salt (MTT) metabolic assay.—(see also: Schwartz, O., et al., AIDS Rcs. Hum. Retroviruses, 4 441–448, 1988). This assay reveals 50% cytotoxicity of SAM-AZT at 2.5×10$^5$ nM ($^-$15.5 μg/mL complex SAM-AZT) providing a selectivity ratio in vitro of almost 7100, revealing a very high therapeutic index of this particular molecular complex. Quite surprisingly, the same therapeutic index cannot achieved by administrating the equivalent amounts of SAM and AZT alone, or by administrating the two compounds as loose combination, nor following or giving the one prior to the other, respectively. In this case the therapeutic index decreases to 5,100 when administering SAM first and AZT second. However, adding e.g. AZT in concentrations which are equivalent to those found in the molecular complexes, reveal no statistically significant results prior to those mentioned above. Furthermore, and more importantly at the administered dose of AZT in this assay system as well as in man this dose can be regarded to be in the cytotoxicity regime of AZT already.

ADVANTAGE OF THE MOLECULAR COMPLEXES

SAM is a natural occurring molecule with a high metabolic potential in methyl transfer. It is known that certain receptors can act as catalysts for the transfer of a methyl group from a sulfonium compound to a nucleophile. Such a reaction is very common in nature when the alkylating agent is SAM, or a complex between SAM and another biological active molecule, e.g. 3'-azido-2'-dideoxynucleosides acting as a whole molecular entity and supporting synergistic effects. The nucleophiles in these reactions can be of a broad range of structures including RNA and DNA, protein, sugars and C=C bonds of steroids and lipids, all components relevant for the inhibition of HIV replication. The similarity of the structure of our claimed compounds endorses the view of cation π-interactions which might be the important and underlying structure with respect to various reactions. This is, e.g. supported by the crystal structure of a cytosine-DNA methyltransferase (see e.g. Cheng, X., et al., Cell, 74, 299, 1993), revealing van der Waals contact between the S—CH$_3$ unit and the π-face of a tryptophan residue in a favorable alignment for catalysis assisted by these cation-π interactions, very similar as observed and described for the SAM≈ddN-N$_3$ complexes. Finally one would expect that the tendency of aromatic residues from integral membrane proteins to cluster near the surface of the membrane could reflect partly cation-π interactions between the aromatic ring and the choline head groups of the lipid. In addition SAM is known to play an integral part in the methylation of choline. The same structural motif can be accounted for the proposed molecular complexes, yielding the typically quadrupole π-cations with the novel activities as described here, by possibly expanding the possibilities of the metabolic or biochemical transfer of methyl groups.

We have demonstrated that it is possible to improve the efficiency of ddN without bypassing the phosphorylation step. It is known that that phosphorylated derivatives are not likely to cross membranes efficiently, which might be possible in the presence of SAM, thus reaching the molecular targets. These described molecular complexes comprising of SAM and 3'-azido-2'-dideoxynucleosides do have the advantage not acting as a prodrug nor as a loose combination but inhibiting the HIV-replication by a complete, not yet known and different mechanism very efficient, and avoiding the usual side effects associated with the dideoxynucleosides. Moreover, e.g. SAM-AZT as well as SAM-UZT, respectively, have been found less toxic than AZT for bone marrow stem cells, and less toxic as well as inhibitory to mitochondrial DNA replication.

Although results from in-vitro assays are sensitive and significantly variables in clinical trials and pharmacological studies as shown for AZT and ddC which are the most potent inhibitors of RT or against HIV infections, these nucleoside analogs produce as mentioned above severe side effects. The observed peripheral neuropathological effects upon prolonged administration of AZT or ddC, respectively, leading also to anemia due to the build up of thymidine monophosphate by competitive inhibition of thymidylate kinase. The resultant depletion in thymidine triphosphate pools in host cells starves host DNA biosynthesis. Furthermore, a rash which subsided with continued therapy has also been noticed. The present molecular complexes are expecting to reduce these severe side effects drastically because of the observed reversal of the inhibition of the thymidylate kinase due to the presence of SAM as shown in in-vitro experiments.

Furthermore the efficiency of such molecular complexes is also seen on the rate at which they are metabolized intra cellularly to the corresponding free ddNMP available to be further transformed to the triphosphate derivative active on the RT, which is enhanced due to these molecular complexes as shown through the kinetics in-vitro and in-vivo. In order to make this transformation feasible, the unique and stable molecular conformation of these complexes and their solvation facilitates the inhibitory and regulatory effects on RT, lipid penetration and inhibitory effects on the growing infective RNA or DNA polymeric chains. The avoidance of e.g. AZT-monophosphate accumulation, similarly also for other ddN $N_3$ compounds, which causes severe inhibition of cellular dTMP kinase, resulting in a blockade of further phosphorylation steps, while on the contrary, the disclosed molecular complexes, appear to be unable to induce the same effects and is clearly incapable of inhibiting their own phosphorylation. This is completely different from those of the single administration of the components, e.g. SAM and ddN≈$N_3$. For these reasons it seems clear that increasing the concentration of e.g.AZT-MP is of little value while by contrast, e.g. SAM-AZT does not accumulate, but being readily converted to the triphosphate derivative. This is also endorsed by the findings that the kinetics of inhibition on the RT enzyme is influenced by the presence of inorganic phosphate resulting in restoring active ATP during the presence of SAM. The apparent triphosphatase activities which have been noticed during the performance of the assay kinetics of the complexes in the presence of RT, can be stimulated only through SAM in the presence of phosphate ($P_i$), not by the 3'-azido-2'-dideoxynucleotides and their analogs. Furthermore, the stimulation of the triphosphatase activity by SAM seems to enhance the onset of the inhibitory action of the nucleosides analogs when added as molecular complexes to the enzymatic system. Experiments conducted in the presence of the loose combination of SAM and the nucleoside analogs did not show this activation. This interference in stimulation of various components is also been noticed in the evaluation of the response to IL-β, IL-2 and IL-6 as well as interferon-γ upon administration of these molecular complexes.

In order to determine the stability of these complexes in physiological conditions, the half-life times of the compounds were estimated in human plasma after separation on a chiral column and using a HPLC apparatus applying, monitoring the fluorescence of both components at 310 nm (excitation at 278 nm) after complete separation of the two peaks. All molecular complexes according to scheme I tested were neither being degraded chemically, particularly not SAM, nor susceptible to attack by plasma enzymes revealing half-life times of 2–3 h for AZT depending on the amount of load of the complex with AZT, which means the dose of the SAM-AZT complex. Whereas for SAM, e.g. in the AZT-SAM complex, we determine a half-lifetime of more than 10 h, in the average of 12 h and normally independent of the amount of load of the SAM≈ddN-$N_3$.— Note: pharmacokinetic studies of AZT indicate a plasma half-life of AZT of approx. of 1 h, thus necessitating frequent administration in order to maintain therapeutic drug levels. Due to the molecular complexes it is possible to reduce the number of administrations drastically and even reduce the dose of the nucleoside analog by reducing the total amount of the molecular complex, when given to the patient. Furthermore, these effects cannot achieved by a loose combination of both compounds, nor separately after administrating of SAM and then AZT, or vice versa. Pauwels et al. (Nature, 343, 470–474, 1990) has shown that ddN and ddN analogs have apparently no effect on the HIV replication when added more than 6 h after cell infection, and as these drugs including prodrugs display half-lives largely over the 6 h limit, would suggest that the compounds, e.g. SAM are internalized into infected cells rapidly and intracellularly yielding the metabolized biochemically active entities, particularly in the presence or due to the presence of SAM and ddN-$N_3$ tailored as molecular compounds. As it has been shown for AZT high dosages are needed to guarantee penetration into the CSF as well as for SAM which has long been known, in order to achieve levels of AZT of approximately 35–70% of the plasma concentrations after administration of 2.5 and 5 mg/kg doses, respectively. As mentioned before and according to these data, it can be suggested that higher doses of AZT should be administered to achieve adequate higher antiviral concentrations over a long period of time in the CSF. But the increased dose level, however, resulted in bone marrow toxicity. Moreover, most importantly AZT does not penetrate into the brain tissue from the CSF and therefore may not suppress viral replication in the brain.

These molecular complexes overcomes not only the problem of rapid elimination and decreased permeability of 3'-azido-2',3'-dideoxynucleosides and corresponding analogs through the blood-brain barrier, but also to increase the therapeutic efficacy for treating HIV infections and ARC. The achievements in inhibiting HIV replication, and the AIDS related secondary infections and diseases, particularly the neurological disorders upon administration of these molecular complexes, by reducing the severe side effects, especially those of anemia and leucopenia, as seen normally from taking the nucleosides analogues are the main advantages of this new class of substances.

The molecular complexes of the invention are also useful as positive controls in assays aimed at developing other HIV reverse transcriptase inhibitors. More specifically, these molecular complexes can be used in reverse transcriptase inhibition assays to establish that the assay system is functioning properly.

EXAMPLES

Preparation of the (+)-SAM-3'azido-2',3'-dideoxythymidine complex.

1.-Preparation of the Hydroxo form of (+)-SAM [(+) SAM OH].

10.0 g of (+)-SAM-hydro-chloride containing normally one to two molecules of water has been dried under vacuum (0.010–0.015 bar) at 100° C. for 24 h until constant weight has been achieved. The R-(+)-SAM-chloride obtained has a molecular weight of 434 as determined by FAB-MS methods, using glycerol and thioglycine as matrix. The FAB ionization was obtained with a FAB field source operated with Argon at 8 kV and 1.5 mA. Cesium iodide was used for calibration; accelerating voltage was 8 kV (Finnigan 8020). The apparent, and working molecular weight of the hydrochloride of (+)-SAM was found to be 489 (FAB MS 490 m/e [M+H]$^+$), upon controlled drying only 433, consisting with differential thermogravimetric results. Thus for the starting material as the hydrochloride the apparent molecular weight is 489 (FAB MS m/e 490 [M+H]$^+$), consisting with a composition of (+)-SAM•Cl•HCl•H$_2$O, whereas the dried compound is consistent with a composition as SAM•Cl. These molecular weights of the different SAM-salts which have been confirmed by vapor osmometry and FAB-MS using different matrices or solvents, respectively, are essential for calculating the real stoichiometric amounts of the 3'-azido 2'-deoxynucleosides needed for preparing the desired molecular complexes between SAM and the 3'-azido-2'-dideoxynucleosides.

1.0 g of R-(+)-SAM•Cl was dissolved in 0.01 M sodium bicarbonate (100 mL) at 5° C. and loaded onto an ion-exchange column (2.5×150 cm) which was filled with Dowex-1-Cl$^-$, 100–300 mesh, or the SAM-Cl, dissolved in saline can be loaded directly onto the ion exchange column, pH 5.5. Separation of the chloride from SAM was performed by eluting the column with 0.2 M NH$_4$ OH in the presence of 0.0025 M Na$_2$ CO$_3$ (chloride free) at 5° C. or 20° C., respectively. The same elution can be performed applying a formiate system and eluting the (+)-SAM-OH in the presence of the same NH$_4$OH buffer as described above, keeping a pH of 10, or applying Na$_2$ CO$_3$ (0.05 M) in the presence of 0.01 M NaHCO$_3$. The elution was carried out at a rate of 0.25–0.30 mL/min, using the above mentioned conditions. Another method for producing large quantities of SAM-OH, and applying a higher effluent rate than 0.25 mL/min, e.g. of 50 mL/min the Dowex-Cl-column was loaded with the same amount of the SAM-Cl, but eluted in the presence of 0.01 M TRIS-OH at pH 8.5 (5° C.). The peak profile was monitored at 260 nm, the exchange of chloride vs. the hydroxide of SAM was measured in the eluent by means of a chloride sensitive electrode. Normally the chloride eluted first and after approx. 200 mL of eluting buffer the SAM-OH appears in the elution volume. Upon concentration by means of slow evaporation of the water under vacuum, the material was recrystallized from EtOH/isopropanol (80/20 v/v), washed with ether or petrol-ether, and the precipitate dried over CaCl$_2$ in vacuum. Chemical yield: 0.85 g, 85% yield, having an optical purity 95%, [α]$_{560}$ +56 (C=1.5, water, 20° C.), m.p.>210° C. (dec.). Chemical analysis: C, H, N, O, H, S: 43.36%, 5.81%, 20.22%, 23.10% , 7.77%. C$_{15}$H$_{24}$N$_6$O$_6$ S. ε=11,650 (265 nm, water). FAB MS m/e 416 [M+H]$^+$. Also FAB MS m/e 438 [M+Na]$^+$. IR (KBr); 3268 cm$^{-1}$, OH.

Another preparation of the hydroxide form of (+)-SAM uses SAM-tosylate•HSO$_4$•H$_2$SO4 as starting material, precipitating the sulfate in acid solution at 5° C. (0.01 M HCl) in the presence of Ba(OH)$_2$ (0.001 M) under continuous stirring as the sulfate, low speed centrifugation ($^-$1000 rpm), and subjecting the supernatant to several fractional crystallizations using EtOH-2-propanol mixtures with different ratios as 40/60% v/v→90/10% v/v.

Using (+)-SAM-HSO$_4$•H$_2$SO$_4$ as starting material the same procedure as described for the precipitation with Ba(OH)$_2$ or BaCl, can be applied in aqueous solutions at room temperature maintaining a solution pH of 8.0.

2.—Formation of the (+)-SAM-3'-azido-2 ',3'-dideoxythymidine complex.

A 150 mL neck flask equipped with a mechanical stirrer and thermometer was charged with 20 mL H$_2$O and 4.15 g (+)-SAM-OH (0.01 mole) under nitrogen at 20° C. The mixture was agitated until a solution was obtained, normally within 1 to 2 minutes. It is essential that the aqueous solution is transparent and not colored, e.g. should not turn into a yellowish solution after a couple of minutes. The UV-absorbance spectra recorded for this solution should be identical with the starting material upon dilution to measure the molar absorption coefficient in order to avoid any dimerization of SAM or production of S-adenosylhomocysteine or D-ribosylmethionine and L-lyxosylmethionine, respectively, since S-adenosylmethionine in the hydroxide form is approx. 10$^2$ to 10$^3$-fold more reactive towards polarizable nucleophiles, e.g. oxygen, than the chloride or the sulfate. A solution of (+)-3'-azido-2',3'-dideoxythymidine (AZT) in ethanol-water (50/50%v/v) (2.68 g, 0.01 mole in 40 mL ethanol-water) was made up, and added through a dropping funnel to the aqueous SAM-OH solution over a period of time of 10 min. at a temperature of 35° C. The solution was left under continues stirring for a period of time of 45 to 60 minutes in the presence of ammonium azide, which has been added at a concentration of 0.015 mole dissolved in ethanol-water (50/50 v/v) through another dropping funnel when adding the solution of AZT. The solution was cooled down to 0–5° C., where normally a fine crystalline precipitate developed, or the solution is being concentrated by rotary evaporation (bath temperature $^-$50° C.) in vacuum to 25% of its original solution, and subsequently cooled to 5° C. Upon addition of EtOH or ethyl acetate a fine precipitate appears either at room temperature or at 5° C. Adding more cold EtOH (100%) under continuous stirring for approx. 30 min., the turbid solution was filtered off, the supernatant concentrated, and subsequently seeded with small crystals of the SAM-AZT salt. The resulting solution in the presence of the seeds and additional EtOH (100%) was aged at 20–30° C. for about 1 h with agitation, cooled to 0–5° C. and held for 2–3 hours. The product was filtered off, washed with 5° C. EtOH, and dried in vacuo at 20° C. over CaCl$_2$, or MgSO$_4$ yielding different compounds with different degree of hydration.

The sample of SAM-AZT crystallized from EtOH-water solutions and dried over CaCl$_2$ contains about 6 water molecules, whereas the sample of SAM-AZT crystallized from EtOH or ethyl acetate contains only two water molecules as determined from thermogravimetric measurements and powder X-ray diffraction experiments.—However, upon rapid drying over CaCl, and MgSO$_4$ in vacuo at 25° C., respectively, a compound is obtained which is indeed hygroscopic, but does not contain any measurable amounts of interstitial water within the crystalline lattice.

Dried sample of SAM-AZT (in the OH form): Chemical yield 86%, chemical analysis: C, H, N, O, S, as determined to 43.98%; 5.46%; N, 22.58% ; O, 23.43% and S, 4.69%. C$_{25}$H$_{37}$ N$_{11}$O$_{10}$S. FAB MS m/e 684 [M+H]$^+$. m.p. 178° C. (dec.). [α]$^{20}$+31 (C=1.0 water). IR (KBr) 3278 (OH), 3421 (NH), 2107 (N$_3$), 1686, 1653 (CONH) cm$^{-1}$. UV$_{max}$ (methanol) 218 nm (ε 12 530) (see Table II).

SAM-AZT with 2 water: Chemical yield 89%, chemical analysis: C, H, N ,O, S, as determined to: 41.78%; 5.75%; 21.44%; 26.71%; 4.46%. $C_{25}H_{41}N_{11}O_{12}S$. FAB MS m/e 720 $[M+H]^+$. m.p. 150° C. (dec.). $[\alpha]^{20}+31$ (C=1.0).

SAM-AZT with 6 water: Chemical yield 89%, chemical analysis : C, H, N, O, S, as determined to: 37.97%; 5.99%; 19.50%; 30.35%; 4.06%. $C_{25}H_{47}N_{11}O_{15}S$. FAB MS 792 $[M+H]^+$. m.p.127° C. (dec.). $[\alpha]^{20}+31$ (C=1.0). Molecular weight determined by vapor osmometry: $M_n$=789±25.

Another method to prepare SAM-AZT uses as starting material SAM•$HSO_4$•$H_2SO_4$ or the tosylate in the presence of the stoichiometric amounts of AZT. 5.93 g (0.01 mol) of (+)-SAM•$HSO_4$•$H_2SO_4$ dissolved in 150 mL water under mechanical stirring and temperature controlled at 20° C., is treated with 0.02 M Ba(OH)$_2$ under nitrogen in the presence of 10%(,(v/v) methanol. 2.67 g AZT, dissolved in 50 mL methanol (100%), is being added through a dropping funnel into the reaction mixture. The developed precipitate is filtered off, the supernatant subsequently concentrated by rotary evaporation by half of the remaining volume. To the clear and concentrated solution 100 mL of ethyl acetate or methanol has been added over 5 minutes without raising the temperature above 20° C. The turbid solution was seeded with SAM-AZT salt crystals (20 mg) and additional 40 mL of methanol or ethyl acetate was added over 20 min. The resulting suspension was aged at 20–25° C. for 1 hour with agitation, cooled to 0–5° C. and held for 1 hour. SAM-AZT was filtered, washed with cold methanol. and dried in vacuo (25° C.) to yield 5.66 g (84%) of SAM-AZT.

All other molecular complexes comprising of (+)-SAM and the appropriate 3'-azido-2',3'-dideoxynucleosides as shown in Scheme I follow this route for preparation. The results and characteristics of these salts are listed in Table II.

For preparation of the title compound having no OH or Cl, respectively, of SAM included in the molecular complexes, the following procedure produces good chemical yields and highly optically active materials.

A 150 mL round bottom necked flask equipped with two dropping funnels, an inlet for $N_2$, stirrer and thermometer is charged with 50 mL of a ethanolic solution (100% EtOH) containing 4.15 g SAM-OH, a slurry of $Ag_2O$ (2.0 g in 15 mL EtOH, dry) is being added under $N_2$ into the well stirred SAM-OH solution. Through another dropping funnel, a ethanolic solution of AZT (2.68 g in 20 mL) is added over a period of time of 15 min. The reaction is completed within 1 h, the silver components are filtered off, the supernatant is being concentrated by ratatory evaporation until a fine precipitate appears. Precipitation is completed by leaving the solution at 5° C. for 4 h. Seeding of the left mother liquid with small crystals of SAM-AZT speeds up crystallization. Upon drying of the crystalline material over $CaCl_2$ in vacuo at 50° C. yielded a material having a m.p. of 178° C. (dec.). Chemical analysis: C, H, N, O, S: 45.11%; 3.79%; 23.48%; 21.97%; 48.18%. FAB MS m/e 667 $[M+H]^+$. IR (KBr) 3421 (NH), 2109 ($N_3$), 1686, 1653 (CONH).Chemical yield .85%

EXAMPLE 2

The following example illustrates the incorporation of the molecular complexes into pharmaceutical compositions and methods of treatment and such are not to be considered as limiting the present novel salts set forth in the claims.

A.—Dry filled capsules containing 250 mg of SAM-AZT per capsule:

| Ingredient | Amount Per Capsule (mg) |
|---|---|
| SAM-AZT | 250.00 |
| Magnesium Stearate Impalpable Powder NF | 5.00 |
| Mannitol, Anhydrous | 5.00 |
| Hard Gelatin Capsule #0 | 40.00 |
| Total Weight of the Capsule | 300.00 |

B.—Film Coated Tablet Containing 200 mg of SAM-AZT per Capsule.

| Ingredient | Amount Per Capsule (mg) |
|---|---|
| SAM-AZT | 250.00 |
| Povidone USP | 10.00 |
| Avicel PH 102 | 10.00 |
| Magnesium Stearate Impalpable Powder NF | 5.00 |
| Core Tablet Weight | 275.00 |
| Hydroxypropyl Methylcellulose | 5.00 |
| Hydroxypropyl Cellulose LF NF W/< 0.3% $SiO_2$ | 4.50 |
| Talc USP Purified | 0.50 |
| Magnesium Sulfate | 5.00 |
| Polyethylen Glycol MW 1000 | 5.00 |

Actual Weight of 300 mg Includes the 5% Hydration of Active Ingredient During Granulation.

| | |
|---|---|
| SAM-AZT | 250.00 |
| $SiO_2$ | 10.00 |
| Hydroxypropyl Methylcellulose | 10.00 |
| Polydimethylsiloxane, MW 17,000 | 5.00 |
| Cetylalcohol | 5.00 |

Actual Weight of 280.0 mg includes the 5% Hydration of Active Ingredient During Granulation.

| | |
|---|---|
| SAM-AZT | 250.00 |
| Simeticone | 20.00 |
| Mannit | 10.00 |
| Magnesium Stearate | 10.00 |
| Cellulose, microcrystalline | 10.00 |

1000 tablets each containing 200 mg of SAM-AZT are produced from the following ingredients:

| | |
|---|---|
| SAM-AZT | 200.00 g |
| Corn Starch | 50.00 g |
| Lactose | 100.00 g |
| Avicel (microcrystalline cellulose) | 150.00 g |
| Magnesium Stearate | 5.0 g |

The SAM-AZT, lactose, and Avicel are admixed, then blended with the corn starch. Magnesium stearate is added. The dry mixture is compressed in a table press to form 1000, 505 mg tablets each containing 200 mg of the active ingredient. The tablets are coated with a solution of Methocel E 15 (Methyl cellulose) including a color if desired containing Yellow No. 6.

| Ingredient | Amount (mg) |
| --- | --- |
| SAM-AZT | 200.00 |
| Mannitol | 100.00 |
| Water for injection q.s. to | 5.00 mL |

The above formulation may be diluted in Sodium Chloride Injection for slow infusion.

Generally all chemicals are of analytical grade according to the standards of the American Chemical Society, and can be obtained from suitable Chemical Companies, e.g. Aldrich or Sigma, respectively. The solvents have been distilled twice under nitrogen, stored over molecular sieves (ZSM-4), and for analytical purposes the solvents were of HPLC grade, so were the ones used for FT-IR and NMR analysis, respectively.

TABLE I

Steady state kinetic parameters for the RT assay system*

| Compound | $K_M$ (nM)** | $K_i$ (nM)** | $k_{cat}$** (min$^{-1}$) | **therapeutic index |
| --- | --- | --- | --- | --- |
| SAM Cl | | | | |
| (1) | 530 ± 20 | 95 ± 35 | 19 | 2.100 |
| (2)+ | 2.300 ± 30 | 820 ± 50 | 15 | |
| SAM ts HSO$_4$ H$_2$SO$_4$ | | | | |
| (1) | 510 ± 20 | 170 ± 30 | 20 | 2.400 |
| (2)+ | 2.500 ± 100 | 700 ± 40 | 18 | |
| SAM/AZT | 670 ± 20 | 180 ± 10 | 1.5 | 7.000 |
| SAM/AZU | 690 ± 15 | 210 ± 10 | 2.1 | 6.500 |
| SAM/AZG | 700 ± 20 | 240 ± 10 | 3.0 | 5.700 |
| SAM/AZI | 410 ± 30 | 130 ± 15 | 2.1 | 5.000 |
| SAM/AZT (AZT (2' - F)) | 500 ± 10 | 100 ± 10 | 2.9 | 7.000 |
| SAM/AZA | 710 ± 20 | 280 ± 20 | 1.7 | 4.500 |
| SAM/AZA (AZT (2' - F)) | 690 ± 10 | 210 ± 20 | 1.7 | 7.000 |

*RT concentrations were determined according to $\epsilon_{279}$ = 335,500 M$^{-1}$ cm$^{-1}$. The second rate order constant for reduction by DTT in this assay system was found to be of the order of 3.1 × 10$^3$ M$^{-1}$ s$^{-1}$, which would interfere significantly with SAM or SAM-adn-N$_3$ compounds, respectively.
**Values determined in triplicate.
†In the presence off 5 mM DTT.

TABLE II

Some physical Characteristics of SAM ~ ddN ≈ N$_3$ compounds

| | | m.p. (° C.) | | | | $\epsilon$ (water), pH 7.0 | |
| --- | --- | --- | --- | --- | --- | --- | --- |
| No | compound | SAM as SAM$^{\delta+}$ | SAM OH | SAM as SAM Cl | $[\alpha]_D^{20}$ | nm | $\epsilon$ |
| (1) | 3'-azido-2',3'-dideoxythymidin (AZT) | 150 | 178 | 121 | +31 (c = 1, MeOH) | 217 265 350 | 12.500 11.300 8.010 |
| (2) | 3'-azido-2',3'-dideoxyuridine AZU) | 125 | 191 | 101 | +91 (c = 2.5, EtOH) | 210 228 278 | 13.750 11.200 9.800 |
| (3) | 3'-azido-2',3'-dideoxycytidine (AZC) | 131 | 168 | 92 | +39 (c = 1.5, Aceton) | 212 235 272 | 12.000 8.700 8.500 |
| (4) | 3'-azido-2',3'-dideoxyadennine (AZA) | 127 | 173 | 111 | +5.6 (c = 2.0, EtOH) | 208 262 355 | 14.000 10.000 9.100 |
| (5) | 3'-azido-2',3'-dideoxyinosine (AZ1) | 141 | 191 | 100 | +71 (c = 2.0, EtOH) | 200 252 350 | 14.500 9.700 5.700 |

TABLE II-continued

Some physical Characteristics of SAM ~ ddN ≈ N₃ compounds

| | | m.p. (° C.) | | | | ε (water), pH 7.0 | |
|---|---|---|---|---|---|---|---|
| No | compound | SAM as SAM$^{\delta+}$ | SAM OH | SAM as SAM Cl | $[\alpha]_D^{20}$ | nm | ε |
| (6) | 3'-azido-2',3'-dideoxyguanosine (AZG) | 135 | 168 | 97 | +15 (c = 3.0, EtOH) | 215 245 333 | 13.900 11.200 9.100 |
| (7) | 3'-azido-2',3'-2'-fluorothymidine | 126 | 145 | 79 | +15 (c = 1.5, MeOH) | 215 265 345 | 12.100 9.100 8.050 |

Noncompetive inhibition of SAM (FIG. 2) and of SAM (FIG. 3) as determined from a double reciprocal plot for inhibition of the reverse transcriptase (RT) with Mg-dATP as variable substrate, [poly (rA): oligo (dT)] was fixed and saturating concentrations. At the two highest concentrations of SAM-AZT, the intercept axis seems to increase with the reaction rates.

We claim:

1. A compound comprising (+)-S-adenosylmethionine (SAM) and a 3'-azido-2', 3'-dideoxynucleoside, or salts of said complex.

2. A compound according to claim 1 wherein the 3'-azido-2',3'-dideoxynucleoside is selected from a 3'-azido-2',3'-dideoxy-pyrimidine.

3. A compound according to claim 1 wherein the 3'-azido-2',3'-dideoxynucleoside is selected from a 3'-azido-2',3'-dideoxy-purine.

4. A compound according to claim 1 wherein the 3'-azido-2',3'-dideoxynucleoside is 3'-azido-2',3'-dideoxy-thymidine.

5. A compound according to claim 1 wherein the 3'-azido-2',3'-dideoxynucleoside is 3'-azido-2',3'-dideoxy-2'-(S)-fluoro-thymidine.

6. A compound according to claim 1 wherein the 3'-azido-2',3'-dideoxynucleoside is 3'-azido-2',3'-dideoxy-uridine.

7. A compound according to claim 1 wherein the 3'-azido-2',3'-dideoxynucleoside is 3'-azido-2',3'-dideoxy-cytosine.

8. A compound according to claim 1 wherein the 3'-azido-2',3'-dideoxynucleoside is 3'-azido-2',3'-dideoxy-adenosine.

9. A compound according to claim 1 wherein the 3'-azido-2',3'-dideoxynucleoside is 3'-azido-2',3'-dideoxy-2'-(S)-fluoro-adenosine.

10. A compound according to claim 1 wherein the 3'-azido-2',3'-dideoxynucleoside is 3'-azido-2',3'-dideoxy-guanosine.

11. A compound according to claim 1 wherein the 3'-azido-2',3'-dideoxynucleoside is 3'-azido-2',3'-dideoxy-inosine.

12. A compound according to claim 1 wherein SAM is SAM OH.

13. A compound according to claim 1 wherein SAM is SAM Cl.

14. A process for preparation of a compound according to claim 1 wherein a salt of (+)-S-adenosylmethionine (SAM) and
a 3'-azido-2',3'-dideoxynucleoside are reacted with each other in the presence of an aqueous solvent containing at least one organic solvent selected from the group consisting of methanol ethanol, acetonitrile, petrolether, and 2-isopropanol, and in the presence of an agent, which is an inert gas, in order to prevent oxidation of SAM and dimerization of SAM.

15. A process according to claim 14 wherein for the preparation of the compound a salt of SAM and
a 3'-azido-nucleoside analog of the formula [ddN=N3 comprising a base selected from the bases contained in scheme 1, part II and the sugar unit contained in scheme 1, part III]

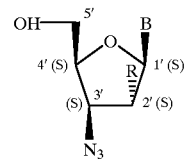

wherein B is a base selected from the group consisting of thymidine, cytosine, guanine, adenine, uracile, and inosine, and R is F or H, are reacted in stoichiometrically equivalent amounts in said aqueous solvent.

16. A process according to claim 14 wherein the salt is selected from SAM•Cl•HCl•H₂O, SAM•HSO₄•H₂SO₄, SAM•tosylate•HSO₄•H₂SO₄.

17. A process according to claim 14 wherein the hydroxide form of (+)-SAM is prepared from (+)SAM•Cl•HCl•H₂O or (+)SAM•HSO₄•H₂SO₄ or (+)SAM•tosylate•HSO₄•H₂SO₄ and then the hydroxide form of (+)-SAM, in said aqueous solvent, is reacted with stoichiometric amounts of AZT in said aqueous solvent.

18. A process according to claim 17 wherein the hydroxide form of (+)-SAM in water is reacted with AZT in an ethanol-water mixture.

19. A method of treating an HIV infection or a symptom of acquired immunodeficiency-related complex in a human comprising administering an effective amount of a compound according to claim 1.

20. A method of supporting the immune system in a mammal comprising administering an effective amount of a compound according to claim 1.

21. A pharmaceutical composition which comprises as active ingredient a compound according to claim 1 and a nontoxic, pharmaceutically acceptable vehicle.

22. A pharmaceutical composition according to claim 20 wherein the active ingredient is present in an amount in the range of from 200 to 500 mg per dose.

23. A process according to claim 14 wherein said agent is nitrogen.

* * * * *